United States Patent

Purcell et al.

[11] Patent Number: 5,350,392
[45] Date of Patent: Sep. 27, 1994

[54] LANCING DEVICE WITH AUTOMATIC COCKING

[75] Inventors: D. Glenn Purcell, Edwardsburg, Mich.; Robert C. Whitson, Osceola, Ind.

[73] Assignee: Miles Inc., Elkhart, Ind.

[21] Appl. No.: 191,123

[22] Filed: Feb. 3, 1994

[51] Int. Cl.$^5$ .............................................. A61B 17/34
[52] U.S. Cl. .................................. 606/182; 128/770
[58] Field of Search ................... 606/181, 182, 185; 128/770; 604/136, 192–198

[56] References Cited

U.S. PATENT DOCUMENTS

| | | | |
|---|---|---|---|
| 4,203,446 | 5/1980 | Höfert et al. | 606/182 |
| 4,527,561 | 7/1985 | Burns | 606/182 |
| 4,637,403 | 1/1987 | Garcia et al. | 606/182 |
| 4,653,513 | 3/1987 | Dombrowski | 128/770 |
| 4,677,979 | 7/1987 | Burns | 606/181 |
| 4,895,147 | 1/1990 | Bodicky et al. | 606/182 |
| 4,990,154 | 2/1991 | Brown et al. | |
| 5,029,583 | 7/1991 | Mesrol et al. | 128/770 |
| 5,074,872 | 12/1991 | Brown et al. | |
| 5,196,025 | 3/1993 | Ranalletta et al. | 606/185 |

*Primary Examiner*—Peter A. Aschenbrenner
*Assistant Examiner*—William W. Lewis
*Attorney, Agent, or Firm*—Roger N. Coe

[57] ABSTRACT

The present invention is a lancing device with an automatic cocking feature. The automatically cocking lancing device utilizes a firing burton loaded with a firing button spring and a drive spring connecting the firing button to a plunger. As the user presses the firing burton and compresses the firing burton spring, the user also moves the plunger until the plunger engages a latching mechanism. The latching mechanism holds the plunger in a latched position, and, as the user continues pressing the firing button, the user compresses the drive spring connected to the plunger. Before firing, the drive spring is compressed enough such that the biasing force of the drive spring is sufficient to cause the plunger to strike and drive a lancet into the user's finger. At that point, the pressing of the firing button causes the lancing device to fife. The plunger unlatches and drives the lancet into the user's finger under the biasing force of the drive spring. At firing, the firing burton spring is compressed, and, once the user releases the firing button, the firing button spring returns the plunger and the firing button to the cocked position under the biasing force of the firing burton spring.

6 Claims, 1 Drawing Sheet

LANCING DEVICE WITH AUTOMATIC COCKING

BACKGROUND OF THE INVENTION

A. Field of the Invention

The present invention generally relates to a new and improved lancing device for puncturing the skin of a user to obtain a blood sample. More particularly, the present invention relates to a new and improved lancing device with an automatic cocking feature.

B. Description of the Prior Art

Sharp pointed lancets are employed to make a puncture or penetration of a patient's skin in order to provide a small outflow of blood. Various tests may be employed with only small amounts of blood so that blood flowing from a finger prick is normally sufficient for these tests. Tests on the blood sample often include contacting a paper strip or reagent pad on a strip carrying chemistry with blood from the wound or puncture.

Known lancet assemblies utilize a hammer or gripper that engages or strikes a lancet and drives the lancet into the skin of a patient or user. By cocking the hammer or gripper, the user compresses a spring that stores energy. As the user cocks the hammer or gripper, the hammer or gripper is latched in position and held in place until the user pushes a firing button. Pushing the firing button releases the hammer or gripper. The hammer or gripper is then driven from its cocked position under the biasing force of the spring to drive the lancet into the patient's skin.

Before the lancet assembly can be used again, the patient or user must cock the hammer or gripper. Current cocking methods require twisting a cap or moving a spring-loaded knob into the cocked position. The device is then cocked and ready to fire. Unfortunately, external cocking methods require extra operating steps, and, unless the lancet assembly utilizes some method to indicate that the device is cocked and ready to fire, the user could be unsure as to whether the lancet assembly is cocked and could accidentally fire the lancet while attempting to cock the hammer or gripper. Moreover, current lancing devices can be prematurely fired by just handling the cocked unit. This is because the firing spring is compressed, and the firing button has a short release stroke.

Current lancet assemblies include two separate components. a reusable base unit and a disposable end cap. An example of such a lancet assembly is disclosed in U.S. Pat. No. 4,990,154, herein incorporated by reference. The end cap is designed to house a lancet, and the base unit houses a hammer that engages or strikes the lancet and drives the lancet into the skin of the patient or user. The hammer acts as a striking element rather than a gripping structure and includes a striking face. The base unit, similar to other prior art lancet assemblies, requires the user to push the hammer into the base unit. As the hammer moves into the base unit, a spring compresses to store energy, and the hammer is latched into a cocked position until the firing button is pressed. After firing, this lancet assembly requires the user to recock the base unit.

Thus, a need exists for an lancing device with an automatic cocking feature so that the lancing device is always cocked and ready to fire. A need also exists for a lancing device which does not fire accidentally and does not misfire.

SUMMARY OF THE INVENTION

The present invention is a lancing device with an automatic cocking feature. The automatically cocking lancing device utilizes a firing button loaded with a firing button spring and a drive spring connecting the firing button to a plunger. As the user presses the firing button and compresses the firing button spring, the user also moves the plunger until the plunger engages a latching mechanism. The latching mechanism holds the plunger in a latched position, and, as the user continues pressing the firing button, the user compresses the drive spring that connects the plunger and the firing button. Before firing, the drive spring is compressed enough such that the biasing force of the drive spring is sufficient to cause the plunger to drive a lancet into the user's finger. At that point, the pressing of the firing button causes the lancing device to fire. The plunger unlatches and drives the lancet into the user's finger under the biasing force of the drive spring. At firing, the firing button spring is compressed and, once the user releases the firing button, the firing button spring returns the plunger and the firing button to the cocked position under the biasing force of the firing button spring. Accordingly, the automatically cocking lancing device of the present invention automatically cocks itself arid, thus, is always cocked and ready to fire. In addition, the drive spring is not fully compressed until the full stroke of the firing button is achieved. Until the latching mechanism releases the plunger at the end of the firing button stroke, the firing button can be returned to the original cocked position, and the drive spring also returns to its uncompressed condition. Accidental misfiring can not occur.

In a preferred embodiment of the present invention, the automatically cocking lancing device is utilized in conjunction with an end cap that houses the lancet. The end cap includes an open end which snaps over a plunger end of the automatically cocking lancing device. The plunger is aligned so that, upon firing, the plunger strikes the lancet and drives the lancet into the user's skin. After firing, the automatically cocking lancing device automatically cocks itself, and the user or patient disposes of the end cap including the contaminated lancet within the end cap or, alternatively, only disposes of the contaminated lancet.

BRIEF DESCRIPTION OF THE DRAWINGS

The advantages of the present invention will become apparent upon reading the following detailed description and upon reference to the accompanying drawings, in which.

DETAILED DESCRIPTION OF THE PREFERRED EMBODIMENT

Figure 1:
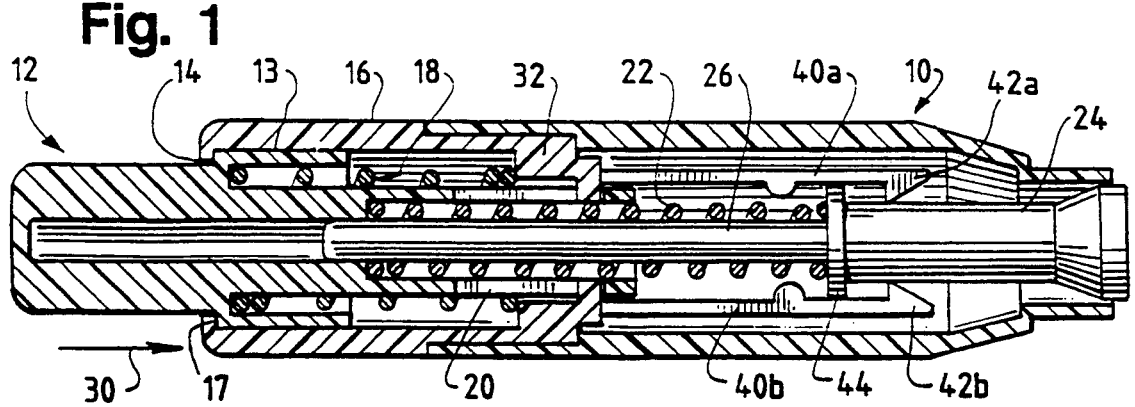
FIG. 1 shows a longitudinal cross-sectional view of the automatically cocking lancing device of the present invention that is cocked and ready to fire.

Referring now to the drawings, and more particularly to FIG. 1, there is illustrated an automatically cocking lancing device of the present invention, generally designated by the reference numeral 10 that is cocked and ready to fire. The automatically cocking lancing device 10 utilizes a firing button 12 movably positioned through a button opening 14 in a casing 16. The firing button 12 includes a firing button sleeve 13 that retains a firing button spring 18. The firing button spring 18 is preferably not attached to but contacts the firing button 12 and the casing 16. As shown in FIG. 1, the firing button spring 18 tends to force the firing button 12 to extend out from the button opening 14 of the casing 16, but a ledge 17 on the firing button 12 maintains the firing button 12 within the casing 16. This extended position for the firing button 12 signals that the automatically cocking lancing device is cocked and ready to fire.

The firing button 12 further includes a latching mechanism release sleeve 20. The latching mechanism release sleeve 20 is preferably positioned about a drive spring 22. The drive spring 22 is preferably attached to the firing button 12 and a plunger 24. The plunger 24 is movably positioned within the casing 16, and the drive spring 22 is preferably positioned about a plunger stem 26 connected to the plunger 24. As shown in FIG. 1, the drive spring 22 tends to force the plunger 24 and the firing button 12 apart. In this way, the drive spring 22 maintains the position of the firing button 12 with respect to the plunger 24 when the lancing device 10 is in the free or firing position of FIG. 1. The plunger stem 26 preferably extends into the firing button 12 and guides the firing and the cocking of the lancing device 10. Specifically, the plunger stem 26 preferably guides the firing button 12, the drive spring 22 and the plunger 24. The plunger stem 26 is preferably fixed to the plunger 24 or integrally formed with the plunger 24, but, alternatively, the plunger stem 26 can movably engage the plunger 24 through a stem opening (not shown) of the plunger 24. In this alternative case, the plunger stem 26 is connected to the fitting button 12.

In the free position of FIG. 1, the automatically cocking lancing device 10 is cocked and ready to fire. The firing button 12 extends out from the casing 16 and, because the firing button has not been pressed, the firing button spring 18 is in its least compressed state, and the drive spring 22 is in a substantially non-compressed state. Thus, in the free position, the stored energy in the firing button spring 18 and the drive spring 22 is at a minimum.

The automatically cocking lancing device 10 is realized by making the firing button stroke (i.e., the displacement of the firing button 12) at least as much as the compressional displacement of the drive spring 22 that is required for the drive spring 22 to force the plunger 24 to drive a lancet (not shown) into the patient's finger. In addition, the displacement of the firing button 12 that results from the user pressing the firing button 12 is at least equal to the compressional displacement of the firing button spring 18 that is required for the firing button spring 18 to automatically cock the lancing device 10. The drive spring 22 connects the movement of the firing button 12 to that of the plunger 24, and, at the end of the firing button travel, the plunger 24 is unlatched to strike and drive the lancet into the patient's finger under the biasing force of the drive spring 22. After fitting, the firing button 12 is released, and the firing button spring 18 forces the firing button 12 back to its cocked position. The firing button spring 18 also forces the drive spring 22, the plunger 24 and the plunger stem 26 back to the cocked position because the drive spring 22 connects the firing button 12 and the plunger 24.

In operation, the user pushes the firing button 12 through the button opening 14 in the direction of arrow 30 and into the casing 16. By moving the firing button into the casing 16, the firing button 12 compresses the firing button spring 18. The firing button spring 18 is compressed between the firing button 12 and a fixed section 32 of the casing 16. Additionally, as the firing button 12 is pressed and moved, the drive spring 22, the plunger stem 26 and the plunger 24 move the same distance in 30 the direction of the arrow 30. Preferably, the plunger stem 26, the plunger 24 and the drive spring 22 move about 0.120 inches before the plunger is held in place.

As previously stated, the drive spring 22 connects the plunger 24 with the firing button 12 and causes the plunger 24 to move with the firing button 12. The drive spring 22 does not begin compressing until latch arms 40a and 40b engage the plunger 24. As illustrated, the latch arms 40a and 40b preferably extend from the fixed section 32 of the casing 16 and are generally parallel to the plunger stem 26. Latches 42a and 42b are formed at the terminal ends of the latch arms 40a and 40b. As the firing button 12, the plunger stem 26, the drive spring 22 and the plunger 24 move in response to the pressing of the firing button 12, the latches 42a and 42b of the latch arms 40a and 40b engage a latch ledge 44 of the plunger 24. Upon the latches 42a and 42b engaging the plunger 24, the plunger 24 is maintained in a latched position and prevented from moving further in the direction of the arrow 30. Consequently, as the user continues pressing the firing button 12, the firing button 12 and the latching mechanism release sleeve 20 continue moving in the direction of the arrow 30, and the firing button 12 commences compressing the drive spring 22 against the plunger 24.

In an alternative embodiment where the plunger stem 26 movably engages within the plunger 24, the plunger stem 26 continues moving in the direction of the arrow 30 through a stem opening (not shown) and into the plunger 24 as the drive spring compresses. In this alternative embodiment, the plunger stem 26 movably engages the plunger 24 and is, thereby, somewhat disconnected from the plunger 24. Therefore, in the alternative embodiment, the plunger stem 26 connects to the firing button 12 so that the movement of the plunger stem 26 also follows the firing button 12, and the firing button sleeve 13 and/or the latch mechanism release sleeve 20 can connect to or are integrally formed with the plunger stem 26.

Figure 2:
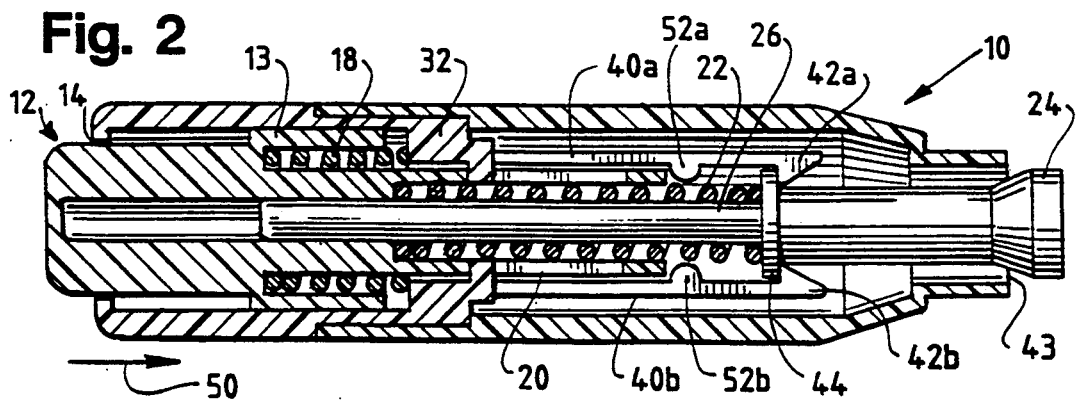
FIG. 2 shows a longitudinal cross-sectional view of the automatically cocking lancing device of FIG. I where the firing button is depressed, and the lancing device is positioned just prior to the point of firing.

After the latches 42a and 42b engage the latch ledge 44 of the plunger 24, the user must continue pressing the firing button 12. The continued pressing of the firing button 12 further compresses both the firing button spring 18 and the drive spring 22. FIG. 2 shows the automatically cocking lancing device 10 in a compressed position just prior to firing. The drive spring 22 is compressed between the firing button 12 and the plunger 24, and the firing button spring 18 is compressed between the firing button 12 and the fixed section 32 of the casing 16. In the compressed position shown in FIG. 2, the firing button spring 18 and the drive spring 22 are at a predetermined engineered compression for the lancing device 10. The compressed drive spring 22 has enough stored energy to drive a lancet into the patient's finger, and the firing button spring 18 has enough stored energy to return the firing button 12, the plunger stem 26, the drive spring 22 and the plunger 24 to the firing position of FIG. 1.

To fire the lancing device 10 shown in FIG. 2, the user must press the firing button 12 still further in the direction of arrow 50. As a result, the latching mechanism release sleeve 20 triggers the unlatching or fixing of the plunger 24. The latching mechanism release sleeve 20 engages latch trigger 52a of the latch arm 40a and latch trigger 52b of the latch arm 40b, causing the latch arms 40a and 40b to spread apart. The spreading apart of the latch arms 40a and 40b also causes the latches 42a and 42b to spread apart from the latch ledge 44 and, thereby, disengage or unlatch from the latch ledge 44 of the plunger 24. Once the plunger is unlatched, the plunger 24 fires out a plunger opening 43 of the casing 16 in the direction of the arrow 50 and under the biasing force of the drive spring 22 to strike and drive a lancet (not shown) into a patient's finger.

After firing, the drive spring 22 is in the non-compressed state, but the firing button spring 18 remains compressed until the user releases the firing button 12. With the firing button spring 18 fully compressed, the lancing device 10 cannot automatically cock because the latch ledge 44 of the plunger 24 will not have passed back through the latches 42a and 42b in the direction opposite to the arrow 50. When the user releases the firing button 12, the firing button spring 18 forces the firing button 12, the plunger stem 26, the plunger 24 and the drive spring 22 in the direction opposite of the arrow 50 and back to the cocked and ready position of FIG. 1.

Figure 3:
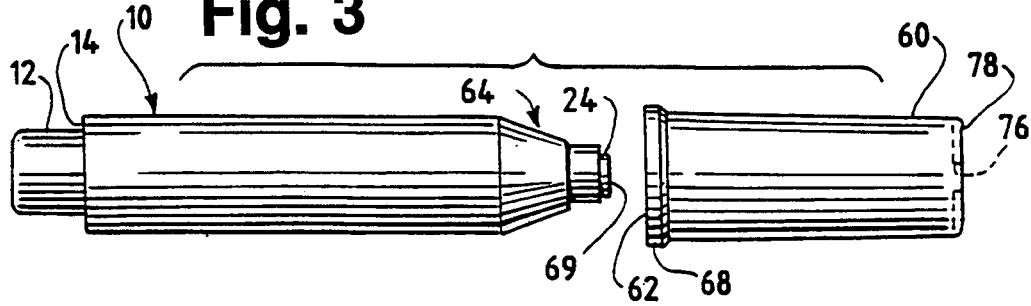
FIG. 3 shows a side view of a lancet assembly including the automatically cocking lancing device of the present invention and an end cap housing a lancet.
Figure 4:
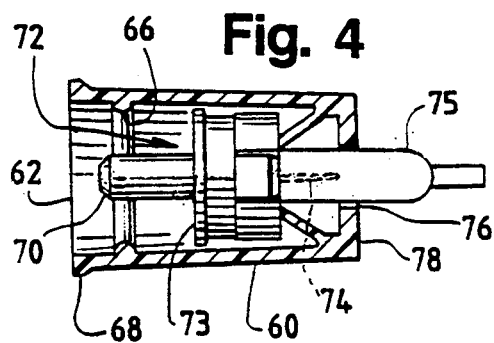
FIG. 4 shows a cross-sectional view of a disposable end cap utilized by the automatically cocking lancing device.

The automatically cocking lancing device 10 can be utilized with a disposable end cap as described in U.S. Pat. No. 4,990,154, herein incorporated by reference. FIG. 3 shows a lancet assembly utilizing the automatically cocking lancing device and an end cap 60 housing a lancet. The disposable end cap 60 includes an open end 62 which snaps over a plunger end 64 of the automatically cocking lancing device 10. As illustrated in FIG. 4, a snap or friction fit can be provided by an inner peripheral rim 66. Alternatively, the inner surface of the end cap 60 can form a wedge fit with the outer surface of the lancing device 10 at the plunger end 64. The engagement of the inner surface of the end cap 60 or the rim 66 with the outer peripheral surface of the lancing device 10 holds the end cap 60 onto the lancing device 10 with the plunger 24 aligned to extend into the open end 62 of the end cap 60.

In the preferred embodiment, the plunger 24 (FIGS. 1, 2 and 3) is hollow, and an open end 69 (FIG. 3) of the plunger 24 aligns with a lancet shank 70 of a lancet 72 that is housed within the end cap 60. In the operation of this preferred embodiment, the user removes a needle plug 75 from a needle 74 of the lancet 72. The user presses the firing button 12 of the lancing device 10, and, as described above, the drive spring 22 forces the plunger 24 out from the casing 16. Under the biasing force of the drive spring 22, the plunger 24 moves towards a striking surface 73 as the lancet shank 70 is inserted within the plunger 24 through the open end 69 (FIG. 3) of the plunger 24 and strikes the striking surface 73 of the lancet 72. Upon striking the striking surface 73, the plunger 24 forces the needle 74 outside of the end cap 60 through an elongated slot 76 of a closed end 78 of the end cap 60 and into the skin of a patient. After firing, the lancing device 10 automatically cocks itself, and the plunger 24 returns to its cocked position.

After blood has been drawn, the user can remove the end cap 60. To allow easy removal of the end cap 60, a flange 68 is formed on the outer periphery of the end cap 60 adjacent to the open end 62. The user removes the end cap 60 merely by pushing against the flange 68 to move the end cap 60 off the plunger end 64 (FIG. 3) of the lancing device 10. After removing the end cap 60, the user disposes of the disposable end cap 60 together with the lancet 72 and loads a new disposable end cap with a new lancet onto the lancing device 10. Furthermore, as shown in FIG. 4, the lancet shank 72 does not extend past the open end 62 of the end cap 60, preventing the accidental exposure of the used needle 74.

Figure 5:
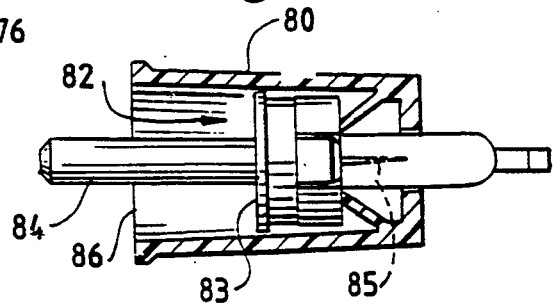
FIG. 5 shows a cross-sectional view of a removable end cap having a disposable lancet utilized by the automatically cocking lancing device.

Alternatively, as shown in FIG. 5, the lancing device 10 (FIGS. 1, 2 and 3) can be used with a removable end cap 80 that houses a disposable lancet 82. The lancing device 10, as described above for the disposable end cap 60, strikes a striking surface 83 of the lancet 82 with the plunger 24 (FIGS. 1, 2 and 3) to force a needle 85 into the patient's skin. Moreover, the removable end cap 80 engages and is disengaged from the lancing device 10 as described above for the end cap 60, but the removable end cap 80 includes a shank 84 of the lancet 82 that extends past an open end 86 of the end cap 80. A used lancet 82 can be easily removed from the end cap 80 by grasping the shank 84 and pulling out the lancet 82 from the end cap 80. Therefore, instead of disposing of both the end cap 80 and the lancet 82, the user only disposes of the lancet 82. Accordingly, after using the lancet 82, the user snaps a new lancet into the removable end cap 80 and places the end cap 80 back onto the automatically cocking lancing device 10.

Additionally, the lancing device 10 of the present invention has been described with a firing button 12 including a firing button sleeve 13 and a latching mechanism release sleeve 20. These structures can be integrally formed as part of the firing button or conventionally connected together. Moreover, the lancing device of the present invention is not limited to the latching mechanism specifically described, and the latching mechanism can be any latching mechanism known in the art. Furthermore, as mentioned above, the present invention encompasses alternative embodiments where the plunger stem movably engages the plunger through a stem opening in the plunger and connects to the firing button. In this alternative embodiment, the firing button sleeve and/or the drive spring sleeve can connect to or are integrally formed with the plunger stem, and the firing button simply connects to the plunger stem.

Thus, the automatically cocking lancing device of the present invention and many of its attendant advantages will be understood from the foregoing description, and various modifications can be made in the form construction and arrangement of the parts thereof without departing from the spirit and scope of the invention or sacrificing all of their material advantages, the form described above being merely a preferred or exemplary embodiment thereof.

What is claimed is:

1. An automatically cocking lancing device, comprising:

a casing having a firing button opening and a plunger opening;

a firing button movably positioned in said casing through said firing button opening;

a plunger movably positioned within said casing;

a firing button spring engaging said firing button and said casing;

a drive spring engaging said firing button and said plunger; and a latch mechanism adjacent to said plunger for engaging said plunger, said firing button engaging said latch mechanism to disengage said plunger.

2. The automatically cocking lancing device of claim 1 wherein said firing button includes a latching mechanism release sleeve, said latching mechanism release sleeve being aligned to disengage said plunger from said latching mechanism.

3. The automatically cocking lancing device of claim 2 wherein said firing button includes a firing button sleeve, said firing button sleeve retaining said firing button spring.

4. The automatically cocking lancing device of claim 1 further comprising a plunger stem extending from said plunger, said drive spring positioned about said plunger stem for guiding said drive spring and said plunger.

5. The automatically cocking lancing device of claim 1 wherein said latching mechanism includes latch arms connected to said casing, said latch arms extending from said casing, each of said latch arms terminating in a latch that engages a latch ledge of said plunger to latch the plunger.

6. The automatically cocking lancing device of claim 5 wherein said latching mechanism includes a latch trigger on each of said latch arms, said latch triggers spreading apart said latch arms upon being engaged by said firing button to disengage said latches from said latch ledge of said plunger and unlatching said plunger.

* * * * *